(12) United States Patent
Stankowski

(10) Patent No.: US 12,324,895 B2
(45) Date of Patent: Jun. 10, 2025

(54) SPARGER DEVICE FOR A BIOPROCESSING SYSTEM AND METHOD OF MANUFACTURING A SPARGER DEVICE

(71) Applicant: GLOBAL LIFE SCIENCES SOLUTIONS USA LLC, Marlborough, MA (US)

(72) Inventor: Ralph Stankowski, Westborough, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 842 days.

(21) Appl. No.: 16/677,889

(22) Filed: Nov. 8, 2019

(65) Prior Publication Data

US 2021/0138219 A1    May 13, 2021

(51) Int. Cl.
*B01F 23/231* (2022.01)
*A61M 39/08* (2006.01)
*A61M 39/12* (2006.01)
*C12M 1/00* (2006.01)

(52) U.S. Cl.
CPC ............ *A61M 39/08* (2013.01); *A61M 39/12* (2013.01); *B01F 23/231265* (2022.01); *C12M 29/06* (2013.01); *C12M 29/08* (2013.01); *A61M 2039/087* (2013.01); *A61M 2207/10* (2013.01)

(58) Field of Classification Search
CPC ........... B01F 23/231265; C12M 23/14; C12M 23/26; F16L 41/021; F16L 47/345; F16L 47/30
See application file for complete search history.

(56) References Cited

U.S. PATENT DOCUMENTS

| | | | | |
|---|---|---|---|---|
| 3,432,188 A | * | 3/1969 | Turner | F16L 33/08 408/92 |
| 5,388,869 A | * | 2/1995 | Suzuki | F16L 47/02 285/915 |
| 5,775,736 A | * | 7/1998 | Svetlik | F16L 47/00 285/133.5 |
| 5,863,472 A | * | 1/1999 | Jones | C02F 3/20 261/121.1 |

(Continued)

FOREIGN PATENT DOCUMENTS

| | | | |
|---|---|---|---|
| AU | 534528 B2 | 2/1984 | |
| DE | 3514028 A1 | 10/1986 | |

(Continued)

OTHER PUBLICATIONS

Corresponding PCT International Search Report and Written Opinion dated Feb. 3, 2021.

(Continued)

*Primary Examiner* — Jonathan M Hurst
(74) *Attorney, Agent, or Firm* — Grogan, Tuccillo & Vanderleeden LLP

(57) ABSTRACT

A sparger device includes a sparge tube having opposed distal ends, an inlet opening, and a plurality of sparge holes along a longitudinal extent of the sparge tube between the opposed distal ends, and a central hub coupled with the sparge tube at a point intermediate the opposed distal ends of the sparge tube, the central hub having a fluid passageway in fluid communication with the sparge tube via the inlet opening.

8 Claims, 6 Drawing Sheets

(56) References Cited

U.S. PATENT DOCUMENTS

| | | |
|---|---|---|
| 6,290,265 B1 | 9/2001 | Warburton-Pitt et al. |
| 2003/0001295 A1 | 1/2003 | Okajima et al. |
| 2004/0108268 A1 | 6/2004 | Liu et al. |
| 2012/0313266 A1 | 12/2012 | Wadman et al. |
| 2014/0191424 A1 | 7/2014 | Cai et al. |
| 2017/0349874 A1* | 12/2017 | Jaques .................. C12M 29/00 |

FOREIGN PATENT DOCUMENTS

| | | |
|---|---|---|
| DE | 202013006194 U1 | 9/2013 |
| DE | 2013006194 U1 | 10/2013 |
| EP | 0803475 A1 | 10/1997 |
| GB | 1226796 A | 3/1971 |
| JP | 5050899 | 4/1974 |
| JP | 2003144876 | 5/2003 |
| JP | 2011515635 A | 5/2011 |
| JP | 201827543 A | 2/2018 |
| JP | 201998239 A | 6/2019 |
| WO | 2014077561 A1 | 5/2014 |

OTHER PUBLICATIONS

Corresponding Japanese Patent Application No. 2022-516363 Office Action dated Jul. 29, 2024.

* cited by examiner

SPARGER DEVICE FOR A BIOPROCESSING SYSTEM AND METHOD OF MANUFACTURING A SPARGER DEVICE

BACKGROUND

Technical Field

Embodiments of the invention relate generally to bioprocessing systems and methods and, more particularly, to a sparger device for single-use bioreactor systems.

Discussion of Art

A variety of vessels, devices, components and unit operations are known for carrying out biochemical and/or biological processes and/or manipulating liquids and other products of such processes. In order to avoid the time, expense, and difficulties associated with sterilizing the vessels used in biopharmaceutical manufacturing processes, single-use or disposable bioreactor bags and single-use mixer bags are used as such vessels. For instance, biological materials (e.g., animal and plant cells) including, for example, mammalian, plant or insect cells and microbial cultures can be processed using disposable or single-use mixers and bioreactors.

Increasingly, in the biopharmaceutical industry, single use or disposable containers are used. Such containers can be flexible or collapsible plastic bags that are supported by an outer rigid structure such as a stainless steel shell or vessel. Use of sterilized disposable bags eliminates time-consuming step of cleaning of the vessel and reduces the chance of contamination. The bag may be positioned within the rigid vessel and filled with the desired fluid for mixing. An agitator assembly disposed within the bag is used to mix the fluid. Existing agitators are either top-driven (having a shaft that extends downwardly into the bag, on which one or more impellers are mounted) or bottom-driven (having an impeller disposed in the bottom of the bag that is driven by a magnetic drive system or motor positioned outside the bag and/or vessel). Most magnetic agitator systems include a rotating magnetic drive head outside of the bag and a rotating magnetic agitator (also referred to in this context as the "impeller") within the bag. The movement of the magnetic drive head enables torque transfer and thus rotation of the magnetic agitator allowing the agitator to mix a fluid within the vessel.

Depending on the fluid being processed, the bioreactor system may include a number of fluid lines and different sensors, probes and ports coupled with the bag for monitoring, analytics, sampling, and liquid transfer. For example, a harvest port is typically located at the bottom of the disposable bag and the vessel, and allows for a harvest line to be connected to the bag for harvesting and draining of the bag. In addition, existing bioreactor systems typically utilize spargers for introducing a controlled amount of a specific gas or combination of gases into the bioreactor. A sparger outputs small gas bubbles into a liquid in order to agitate and/or dissolve the gas into the liquid, or for carbon dioxide stripping. The delivery of gas via spargers helps in mixing a substance, maintaining a homogenous environment throughout the interior of the bag, and is sometimes essential for growing cells in a bioreactor. Ideally, the spargers and the agitator are in close proximity to ensure optimal distribution of the gases throughout the container.

One common type of sparger is generally T-shaped and is connectable to a gas supply line that runs to the bottom of the bioreactor vessel. The sparger extends upwardly into the interior of the vessel/single-use bag to deliver the gas to the culture within the interior volume. This type of sparger is typically manufactured from three component pieces, a vertical hub having a central passageway, and two opposed tube portions having a plurality of longitudinally-spaced holes that form the arms of the T that extend horizontally outward from the vertical hub. The central passageway of the hub is in fluid communication with the opposed tube portions to deliver gas to the tub portions, which is passed into the culture through the holes along the longitudinal extent of the tube portions. Such a sparger is typically manufactured by intersecting a vertical rod and a horizontal rod to form a T-shape, and then molding around the rods to form the hub. The rods are then removed, leaving a T-shaped passageway within the hub. The opposed tube portions are then joined to the hub such that they are in fluid communication with the T-shaped passageway.

Due to the three-piece configuration of the sparger, and the molding method used to manufacture the hub, the gas delivery holes along the opposed tube portions may not be evenly spaced from the hub. That is, the holes on one tube portion may be positioned closer to the hub than the corresponding holes on the opposed tube portion due to the way each tube portion is seated in the hub. This may lead to reverse flow near the hub, which can result in trapped cell debris inside the tube portions. In addition, the sparger may be prone to the buildup of cells/media at the distal end of the tube portions due to dead space in the tube portions beyond the last gas delivery hole. Moreover, as the vertical portion of the hub is not particularly rigid, the sparger may whip around the inside of the bag and contact the impeller, bag and/or sensors, which is undesirable.

In view of the above, there is a need for an improved sparger device that significantly minimizes the likelihood of cell buildup within the sparger, is less prone to deflection, and which can be produced from a variety of materials. In connection with such a sparger device, there is a need for a manufacturing method which achieves more repeatable hole positioning and is simpler and cheaper than existing methods.

BRIEF DESCRIPTION

In an embodiment, a sparger device is provided. The sparger device includes a sparge tube having opposed distal ends, an inlet opening, and a plurality of sparge holes along a longitudinal extent of the sparge tube between the opposed distal ends, and a central hub coupled with the sparge tube at a point intermediate the opposed distal ends of the sparge tube, the central hub having a fluid passageway in fluid communication with the sparge tube via the inlet opening.

In another embodiment, a method of manufacturing a sparger device is provided. The method includes the steps of providing a tube having opposed distal ends and an inlet opening in a sidewall of the tube between the opposed distal ends, inserting a pin into the inlet opening, overmolding around the pin and the tube to from a central hub, and removing the pin to form a feed passageway within the central hub, the feed passageway being in fluid communication with an interior of the tube via the inlet opening.

In yet another embodiment, a bioprocessing system is provided. The bioprocessing system includes a vessel, a flexible bioprocessing bag positionable within the vessel, and a sparger device coupled to a fluid port in the flexible bioprocessing bag, the sparger device including a sparge tube having opposed distal ends, an inlet opening, and a plurality of sparge holes along a longitudinal extent of the sparge tube between the opposed distal ends, and a central hub coupled with the sparge tube at a point intermediate the opposed distal ends of the sparge tube, the central hub having a fluid passageway in fluid communication with the sparge tube via the inlet opening.

In yet another embodiment, a sparger device is provided. The sparger device includes at least one sparge tube having a distal end, and a plurality of sparge holes along a longitudinal extent of the sparge tube, a hub coupled with the sparge tube, the hub having a fluid passageway in fluid communication with a central passageway of the sparge tube for providing gas to the sparge tube, and a cap on the distal end of the sparge tube, the cap having a throughbore in fluid communication with the central passageway of the sparge tube.

DRAWINGS

The present invention will be better understood from reading the following description of non-limiting embodiments, with reference to the attached drawings, wherein below:

DETAILED DESCRIPTION

Figure 1:
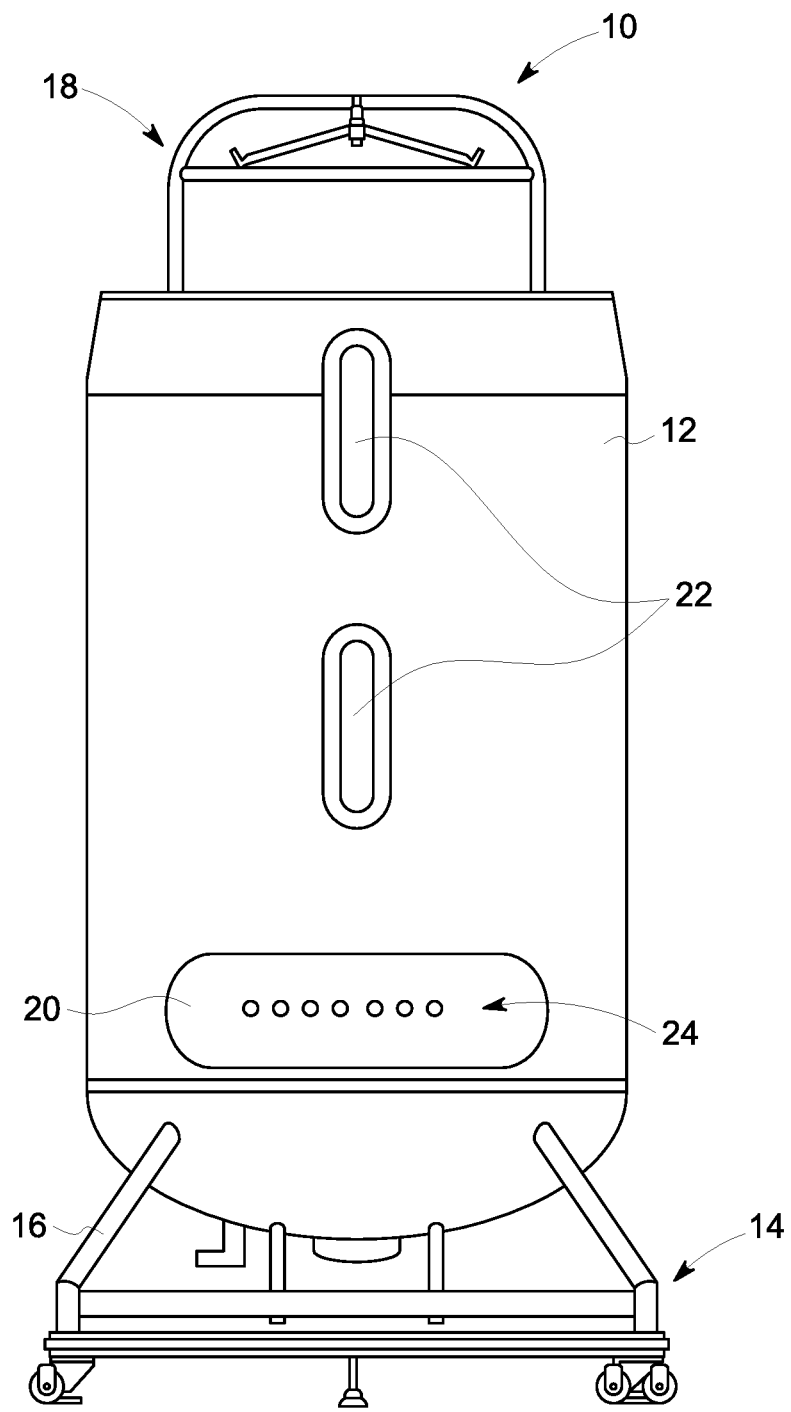
FIG. 1 is a front elevational view of a bioreactor system according to an embodiment of the invention.

Reference will be made below in detail to exemplary embodiments of the invention, examples of which are illustrated in the accompanying drawings. Wherever possible, the same reference characters used throughout the drawings refer to the same or like parts.

As used herein, the term "flexible" or "collapsible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, a rigid container, or a flexible or semi-rigid tubing, as the case may be. The term "vessel" as used herein is intended to encompass bioreactor vessels having a wall or a portion of a wall that is flexible or semi-rigid, single use flexible bags, as well as other containers or conduits commonly used in biological or biochemical processing, including, for example, cell culture/purification systems, mixing systems, media/buffer preparation systems, and filtration/purification systems. As used herein, the term "bag" means a flexible or semi-rigid container or vessel used, for example, as a bioreactor or mixer for the contents within.

Embodiments of the invention provide bioreactor systems and sparger devices for a bioreactor system. In an embodiment, a sparger device for a bioprocessing system is formed as a two-piece assembly and includes a sparge tube having opposed distal ends, an inlet opening, and a plurality of sparge holes along a longitudinal extent of the sparge tube between the opposed distal ends, and a central hub coupled with the sparge tube at an approximate midpoint of the sparge tube, the central hub having a fluid passageway in fluid communication with the sparge tube via the inlet opening. The sparger device is formed by inserting a core pin into an inlet opening in the sparge tube to form an interference fit, overmolding around the core pin and sparge tube to form a central hub, and removing the core pin, thereby providing a feed passageway in fluid communication with the sparge tube via the inlet opening.

Figure 2:
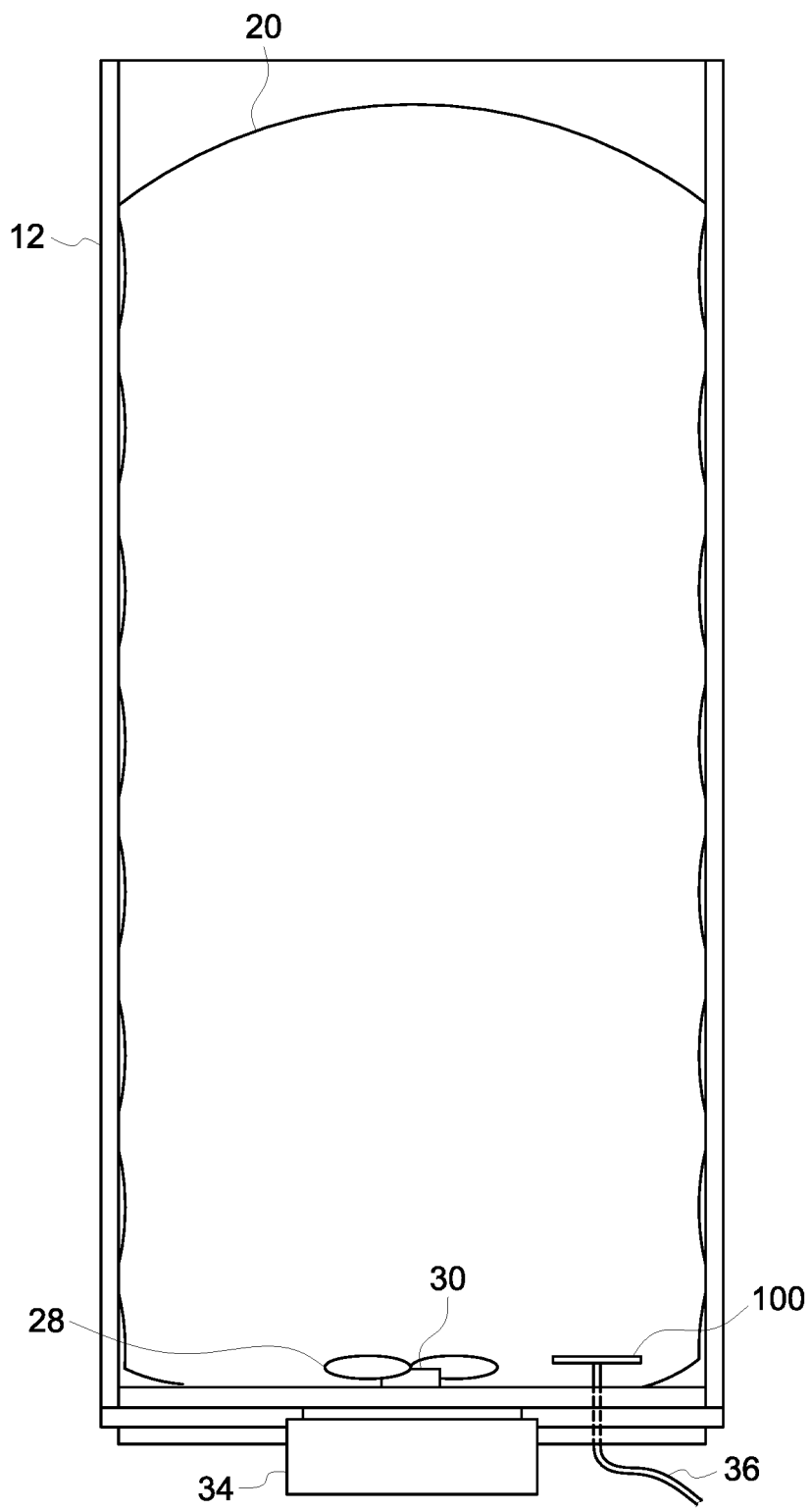
FIG. 2 is a simplified side elevational, cross-sectional view of the bioreactor system of FIG. 1.

With reference to FIGS. 1 and 2, a bioreactor system 10 according to an embodiment of the invention is illustrated. The bioreactor system 10 includes a generally rigid bioreactor vessel or support structure 12 mounted atop a base 14 having a plurality of legs 16. The vessel 12 may be formed, for example, from stainless steel, polymers, composites, glass, or other metals, and may be cylindrical in shape, although other shapes may also be utilized without departing from the broader aspects of the invention. The vessel 12 may be outfitted with a lift assembly 18 that provides support to a single-use, flexible bag 20 disposed within the vessel 12. The vessel 12 can be any shape or size as long as it is capable of supporting a single-use flexible bioreactor bag 20. For example, according to one embodiment of the invention the vessel 12 is capable of accepting and supporting a 10-2000 L flexible or collapsible bioprocess bag assembly 20.

The vessel 12 may include one or more sight windows 22, which allows one to view a fluid level within the flexible bag 20, as well as a window 24 positioned at a lower area of the vessel 12. The window 24 allows access to the interior of the vessel 12 for insertion and positioning of various sensors and probes (not shown) within the flexible bag 20, and for connecting one or more fluid lines to the flexible bag 20 for fluids, gases, and the like, to be added or withdrawn from the flexible bag 20. Sensors/probes and controls for monitoring and controlling important process parameters include any one or more, and combinations of: temperature, pressure, pH, dissolved oxygen (DO), dissolved carbon dioxide ($pCO_2$), mixing rate, and gas flow rate, for example.

With specific reference to FIG. 2, a schematic side elevational, cutaway view of the bioreactor system 10 is illustrated. As shown therein, the single-use, flexible bag 20 is disposed within the vessel 12 and restrained thereby. In embodiments, the single-use, flexible bag 20 is formed of a suitable flexible material, such as a homopolymer or a copolymer. The flexible material can be one that is USP Class VI certified, for example, silicone, polycarbonate, polyethylene, and polypropylene. Non-limiting examples of flexible materials include polymers such as polyethylene (for example, linear low density polyethylene and ultra-low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. In an embodiment, the flexible material may be a laminate of several different materials such as, for example Fortem™, Bioclear™ 10 and Bioclear 11 laminates, available from GE Healthcare Life Sciences. Portions of the flexible container can comprise a substantially rigid material such as a rigid polymer, for example, high density polyethylene, metal, or glass. The flexible bag may be supplied pre-sterilized, such as using gamma irradiation.

The flexible bag 20 contains an impeller 28 attached to a magnetic hub 30 at the bottom center of the inside of the bag, which rotates on an impeller plate (not shown) also positioned on the inside bottom of the bag 20. Together, the impeller 28 and hub 30 (and in some embodiments, the impeller plate) form an impeller assembly. A magnetic drive 34 external to the vessel 12 provides the motive force for rotating the magnetic hub 30 and impeller 28 to mix the contents of the flexible bag 20. While FIG. 2 illustrates the use of a magnetically-driven impeller, other types of impellers and drive systems are also possible, including top-driven impellers.

Figure 3:
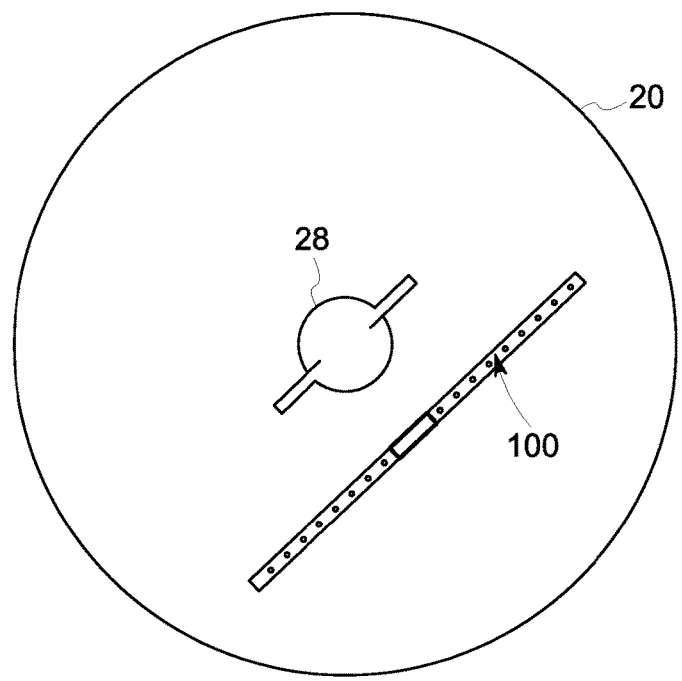
FIG. 3 is a simplified top plan view of the bioreactor system of FIG. 1.

As also illustrated in FIG. 2, the flexible bag 20 contains a sparger device 100 that can be engaged with a port (not shown) on the bottom of the flexible bag 20, which receives a supply of gas from a gas supply line 36. The sparger device 100 extends upwardly into the interior volume defined by the flexible bag 20 and is positioned adjacent to the impeller 28. FIG. 2 is intended to be illustrative of the general configuration and positioning of the sparger device 100. In reality, the sparger device 100 may have a horizontal extent that spans close to the entire inside diameter of the bag 20 and/or vessel 12 (see, e.g., FIG. 3). In addition, it is contemplated that the sparger device 100 may be attached to a port elsewhere on the bottom of the bag (not necessarily adjacent to a periphery of the bottom of the bag 20), or even in a sidewall of the bag 20.

Figure 4:
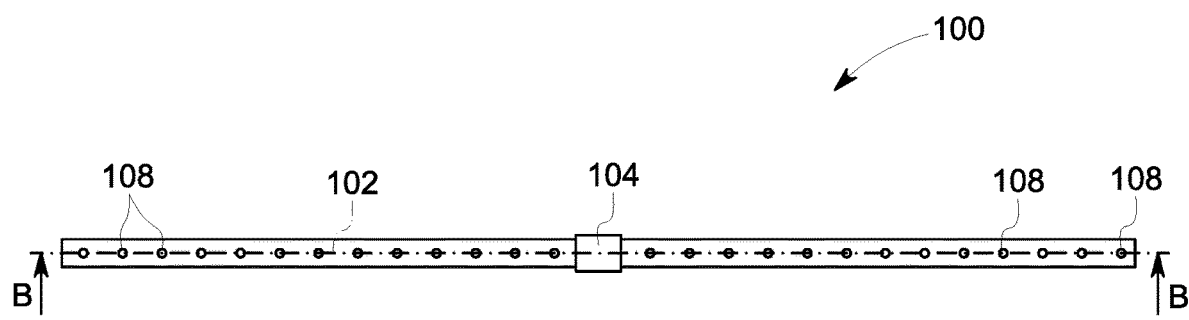
FIG. 4 is a top plan view of a sparger device for use with the bioreactor system of FIG. 1, according to an embodiment of the invention.
Figure 5:
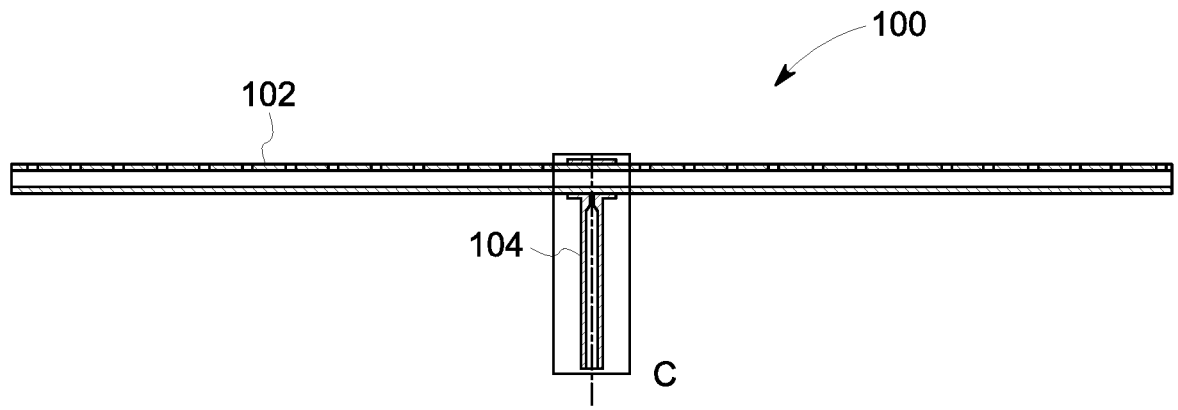
FIG. 5 is a cross-sectional view of the sparger device of FIG. 4, taken along line B-B of FIG. 4.
Figure 6:
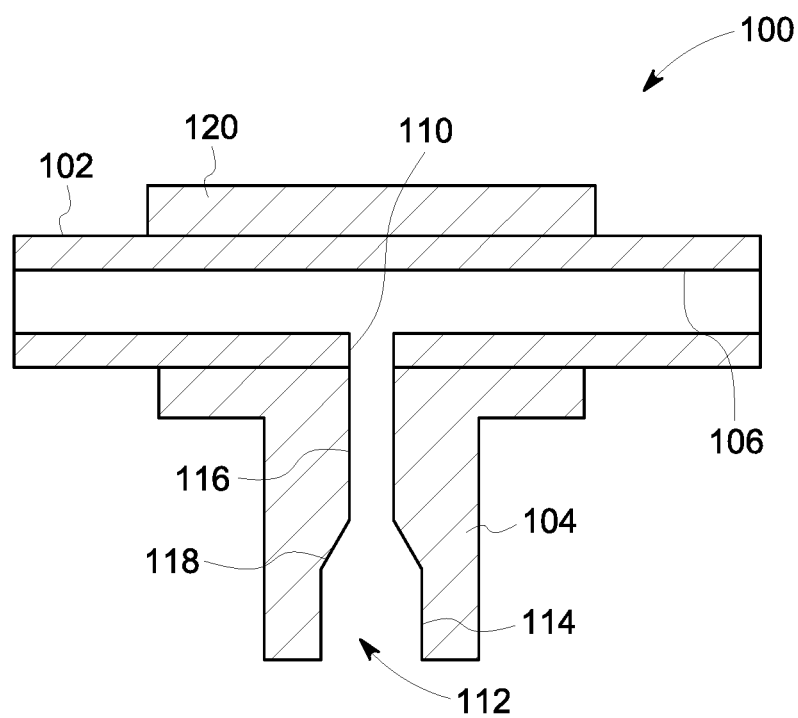
FIG. 6 is an enlarged, detail view of area C of FIG. 5.
Figure 7:
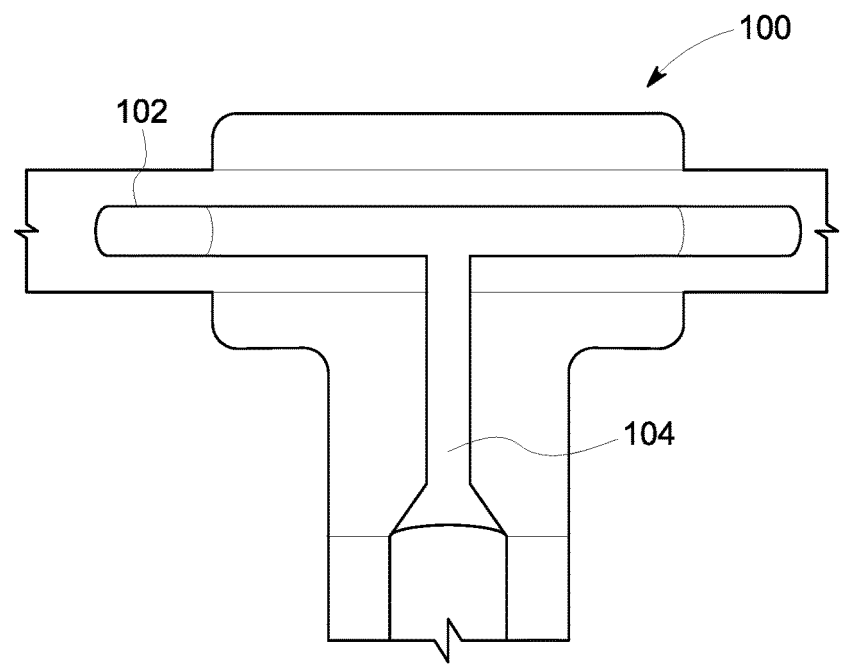
FIG. 7 is an enlarged, side elevational view of the sparger device of FIG. 4.

Turning now to FIGS. 4-6, the sparger device 100 according to one embodiment of the invention is illustrated. As shown therein, the sparger device 100 is generally T-shaped and includes a first tube (sparge tube 102) and a second tube (feed tube 104) connected to, and oriented substantially perpendicularly to, the sparge tube 102. The sparge tube 102 has a central passageway 106 and a plurality of radial sparge holes 108 or apertures along the length of the tube 102 and in fluid communication with the central passageway 106. In an embodiment, the sparge holes 108 are spaced equidistant from one another along the length of the tube 102, although in some embodiments the sparge holes 108 may be irregularly spaced along the tube 102. The sparge tube 102 also includes a central inlet opening 110 in an underside of the tube 102 at a midpoint along the length of the tube 102. In an embodiment, the inlet opening 110 is located approximately 180 degrees from the sparge holes 108 on the top of the tube 102.

As best shown in FIGS. 5 and 6, the feed tube 104 likewise includes a central feed passageway 112 that is in fluid communication with the central passageway 106 of the sparge tube 102 via the inlet opening 110 in the sparge tube 102. In one embodiment, the central passageway 106 may have a large diameter portion 114, a reduced diameter portion 116, and a shoulder portion 118 forming a transition between the larger diameter portion 114 and the reduced diameter portion 116. As illustrated in FIG. 6, the feed tube 104 defines a central hub having a generally T-shaped sleeve 120 that surrounds the sparge tube 102 and serves to connect the sparge tube 102 to the feed tube 104. In an embodiment, the reduced diameter portion 116 of the central passageway 112 of the feed tube 104 and the central passageway of the sparge tube 102 may have an inside diameter between about 0 inches to about 0.25 inches. In an embodiment, the sparge holes may have a diameter between about 0 inches and about 0.25 inches. In another embodiment, the sparge holes may have a diameter between about 0 inches and about 0.125 inches, or about 0 inches to about 0.0625 inches. In an embodiment, the feed tube 104 may have a generally consistent outside diameter of about 0.25 to about 0.5 inches.

While the sparge tube 102 has been described above as being generally linear in shape, it is contemplated that the sparge tube 102 may have almost any shape so long as it is a unitary component. In particular, the sparge tube 102 may be generally annular or arcuate in shape so that it extends adjacent the inner periphery of the flexible bag 20 around the impeller.

As indicated above, the sparger device 100 therefore has a two-piece construction, namely, a unitary sparge tube 102 having the central inlet opening 110, and a feed tube 104 that is in fluid communication with the sparge tube 102 via the central inlet opening 110. It is contemplated that the sparge tube 102 and the feed tube may be manufactured from a variety of materials such as, for example, polypropylene. In an embodiment, the feed tube 104 is manufactured with a wall thickness and/or from a material such that the feed tube 104 is substantially stiff and robust. In an embodiment, the feed tube 104 may be formed by overmolding around the sparge tube 102, as described hereinafter.

Figure 8:
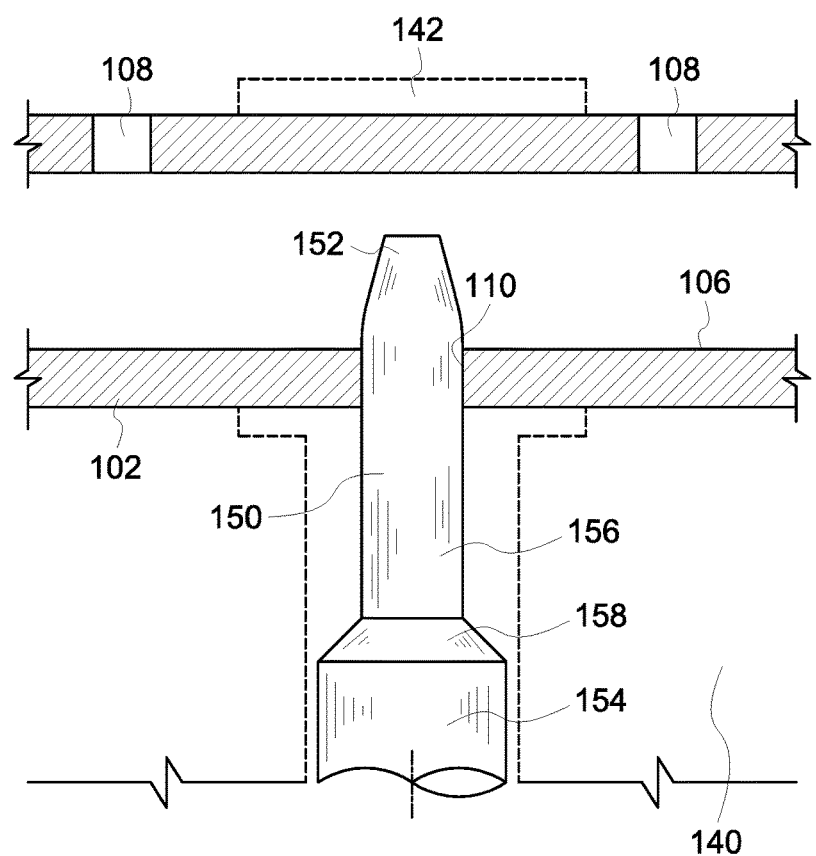
FIG. 8 is a particular, cross-sectional view of a mold assembly used for manufacturing the sparger device of FIG. 4.

In particular, with reference to FIG. 8, the sparger device 100 may be manufactured by first forming the sparge tube 102 with the central inlet opening 110 and sparge holes 108 at predetermined, spaced locations from a midpoint of the tube 102. For example, this can be done using a variety of molding processes, although the invention is not so limited in this regard. In particular, it is contemplated that the sparge tube 102 may be manufactured utilizing a variety of techniques such as, for example, molding or additive manufacturing technologies.

The sparge tube 102, once formed, is then positioned in a mold 140 having a mold region 142 that corresponds in shape/configuration to the shape/configuration of the central hub to be formed. As illustrated in FIG. 8, the mold 140 has a core pin 150; the core pin 150 is inserted into the inlet opening 110 in the sparge tube 102 when the sparge tube is positioned in the mold 140. The core pin 150 has a diameter that is equal to, or slightly larger than, a diameter of the inlet opening 110 in the sparge tube 102. In an embodiment, the core pin 150 may have a diameter that is about 0 to about 0.01 inches and, more particularly, about 0 to about 0.004, and even more particularly, about 0.002 to about 0.004 inches, greater than the diameter of the inlet opening 110 so that the core pin 150 forms an interference fit with the sparge tube 102 when inserted into the inlet opening 110. In an embodiment, the core pin 150 may have a diameter that is slightly (e.g. 0.01 inches) less than the diameter of the inlet opening, which still would prevent the inflow of injected material due to the nominal clearance space. The core pin 150 also has a tapered tip 152 that facilitates insertion of the core pin 150 into the inlet opening 110. As shown in FIG. 8, the core pin 150 has a large diameter portion 154, a reduced diameter portion 156, and a shoulder portion 158 forming a transition between the larger diameter portion 154 and the reduced diameter portion 156.

After the sparge tube 102 is received on the core pin 150 and is positioned in the mold 140, material is passed into the mold region 142 around the core pin 150 and sparge tube 102 to form the central hub (i.e., the sleeve 120 and feed tube 104). The sparge device 100 is then removed from the mold 140. Removal of the core pin 150 forms the central passageway 112 of the feed tube 104. As will be appreciated, receipt of the core pin 150 in the inlet opening 110 of the sparge tube 102 ensures that the holes on opposite sides of the sparge tube 102 are spaced equally from the midpoint of the sparge tube 102. In addition, because the core pin 150 forms an interference fit with the sparge tube 102 when inserted into the opening 110, material is prevented from seeping into the sparge tube 102 through the opening 110, which could form restrictions (which can lead to pressure drops during use) within the passageway 106.

Figure 9:
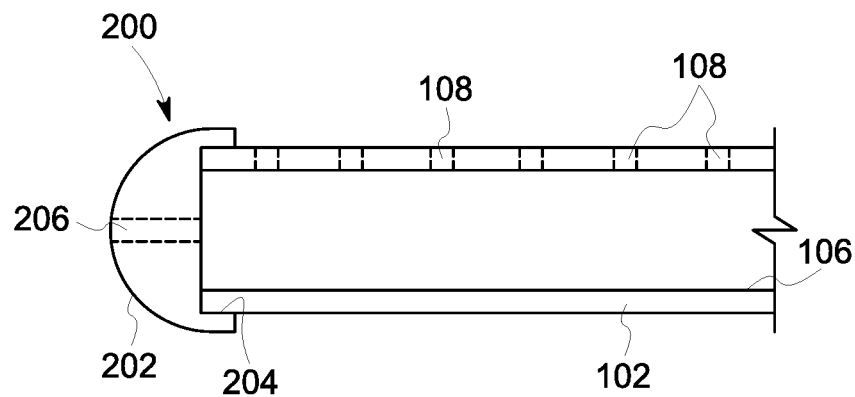
FIG. 9 is a enlarged, partial cross-sectional view of a distal end of the sparger device of FIG. 4, illustrating a cap of the sparger device according to an embodiment of the invention.

Once the sparge device is removed from the mold (or, in some embodiments, prior to overmolding the central hub), the opposed, distal ends of the sparge tube 102 may be plugged or capped. FIG. 9 illustrates a cap 200 for the sparge tube 102 according to one embodiment of the invention. As shown therein, the cap 200 includes a body portion 202 having a cylindrical recess 204 that generally corresponds in diameter to the outside diameter of the sparge tube 102. The cap 200 also includes a central throughbore or hole that is generally aligned with the longitudinal axis of the sparge tube 102 when the cap is received on the distal end of the sparge tube 102. As illustrated in FIG. 9, the cap 200 may be rounded in shape and/or have filleted corners, to minimize or prevent damage to, or scratching of, system components (such as the bag film, impeller, sensors, etc.). In an embodiment, the throughbore 206 has a diameter that is substantially the same as the diameter of the sparge holes 108. The throughbore 206 in the cap 206 allows sparge gas to exit axially through the cap 206 on the distal end of the sparge tube 102. This effectively eliminates any dead space at the ends of the sparge tube 102 beyond the last sparge hole 108.

Figure 10:
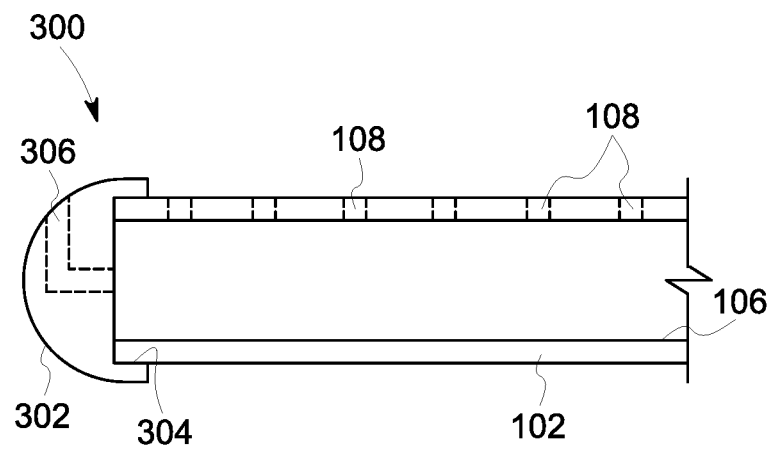
FIG. 10 is an enlarged, partial cross-sectional view of a distal end of the sparger device of FIG. 4, illustrating a cap of the sparger device according to another embodiment of the invention.

FIG. 10 illustrates a cap 300 according to another embodiment of the invention. As shown therein, cap 300 is generally similar in shape and configuration to the cap 200 of FIG. 9, and includes a body portion 302 having a cylindrical recess 304 that generally corresponds in diameter to the outside diameter of the sparge tube 102. The cap 300 also includes a throughbore 306. The throughbore 306 is shaped such that sparge gas exits the cap in a direction generally orthogonal to the longitudinal axis of the sparge tube 102 (i.e., generally parallel to the direction that sparge gas exits through sparge holes 108). For example, as shown in FIG. 10, the throughbore includes a first leg that is generally aligned with the longitudinal axis of the sparge tube 102 when the cap 300 is received on the distal end of the sparge tube 102, and a second leg that forms a substantially 90 degree angle with the first leg. As illustrated in FIG. 10, the cap 300 may, likewise, be rounded in shape and/or have filleted corners, to minimize or prevent damage to, or scratching of, system components (such as the bag film, impeller, sensors, etc.). In an embodiment, the throughbore 306 has a diameter that is substantially the same as the diameter of the sparge holes 108. Similar to the cap 200, the throughbore 306 in the cap 300 effectively eliminates any dead space at the ends of the sparge tube 102 beyond the last sparge hole 108.

It is contemplated that the caps 200, 300 of FIGS. 9 and 10 may be coupled to the distal ends of the sparge tube 102 by various means including, but not limited to, a press fit, adhesive, welding, etc.

Figure 11:
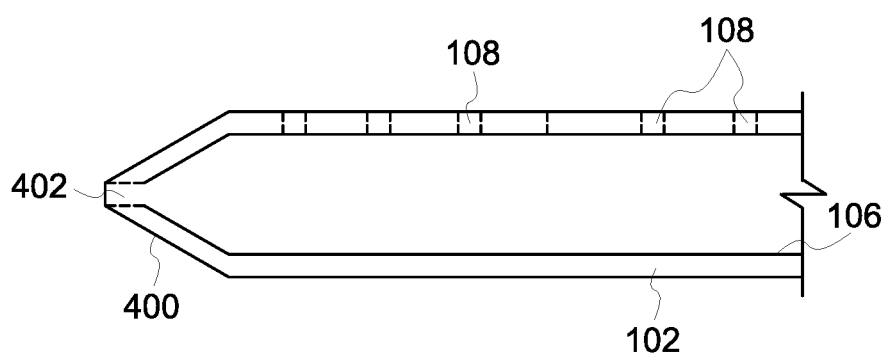
FIG. 11 is an enlarged, partial cross-sectional view of a distal end of the sparger device of FIG. 4, according to another embodiment of the invention.

Turning finally to FIG. 11, in an embodiment, rather than utilizing a cap, the sparge tube 102 may be manufactured with a narrowing distal end 400. In particular, the distal end of the sparge tube 102 may be formed to a point, with an axial opening 402 in the distal end that generally corresponds in diameter to the diameter of the sparge holes 108. Similar to the caps 200, 300 and the holes thereof, the opening 402 allows sparge gas to exit at the terminal ends of the sparge tube 102, preventing any dead space at the ends of the sparge tube 102 beyond the last sparge hole 108.

As alluded to above, the sparger device 100 is intended to be connected to a fluid port on the bottom of the flexible bag 20 of a bioreactor/bioprocessing system. The fluid port, and thus the sparger device 100, are connected to a supply of fluid (i.e., sparge gas) for use during a sparging operation of the bioreactor system. As indicated above, the sparge device 100 is robust and substantially stiff, owing to the two-piece construction of the device, and the configuration of central hub and the feed tube 104. As a result, the sparge device 100 is much less prone to movement within the bag, thereby minimizing the likelihood that the sparge device 100 would contact the impeller, sensors, the bag film, etc. In addition, the provision of an hole or opening on the distal end of the sparger device 100 (via the cap or a narrowing distal end) eliminates dead space beyond the distal-most sparge hole in the sparge tube 102.

The construction of the sparger device 100, and the manufacturing process therefor, also facilitates accurate and repeatable sparge hole position. In particular, the core pin 150, when received in the central inlet opening 110 in the sparge tube 102, precisely positions the feed passage 112 of the feed tube 10 equidistant from the sparge holes 108 to either side of the feed passage 112 and inlet opening 110. Moreover, by utilizing a unitary (i.e., single piece) sparge tube 102, assembly and alignment of the sparge tube 102 (and sparge holes 108 thereof) in relation to the feed tube 104 is simplified. As a result of this accurate sparge hole positioning, the possibility of reverse flow, which can result in trapped cell debris inside the sparge tube, is minimized. The use of the core pin 150, as discussed above, also provides reliable hole seal-off, preventing mold material from seeping into the sparge tube 102, which could create restrictions resulting in pressure drop during sparging.

The sparger device 100 of the invention, and manufacturing method therefor, significantly minimizes the likelihood of cell buildup within the sparger, and is less prone to deflection. The manufacturing method described herein, as discussed above, achieves more repeatable hole positioning and is simpler and cheaper than existing methods. The sparger device of the invention disclosed above may be used for injecting gas into a liquid for a variety of purposes including, for example, to control an amount of dissolved gas (e.g., oxygen, nitrogen, carbon dioxide) in the liquid and/or for carbon dioxide stripping.

In an embodiment, a sparger device is provided. The sparger device includes a sparge tube having opposed distal ends, an inlet opening, and a plurality of sparge holes along a longitudinal extent of the sparge tube between the opposed distal ends, and a central hub coupled with the sparge tube at a point intermediate the opposed distal ends of the sparge tube, the central hub having a fluid passageway in fluid communication with the sparge tube via the inlet opening. In an embodiment, the central hub is overmolded around the sparge tube. In an embodiment, the plurality of sparge holes are located in a top of the sparge tube and the inlet opening is located in a bottom of the sparge tube. In an embodiment, the sparger device also includes a cap on at least one of the opposed distal ends of the sparge tube, the cap having a throughbore in fluid communication with a central passageway of the sparge tube. In an embodiment, the throughbore is an axial throughbore oriented to direct a sparge gas out of the throughbore in a direction generally perpendicular to the sparge gas exiting though the plurality of sparge holes. In an embodiment, the throughbore is oriented to direct a sparge gas out of the throughbore in a direction generally parallel to the sparge gas exiting though the plurality of sparge holes. In an embodiment, the throughbore includes an angle of approximately 90 degrees. In an embodiment, the opposed distal ends of the sparge tube narrow to a point, and the opposed distal ends each include an axial opening for passage of a sparge gas.

In another embodiment, a method of manufacturing a sparger device is provided. The method includes the steps of providing a tube having opposed distal ends and an inlet opening in a sidewall of the first tube between the opposed distal ends, inserting a pin into the inlet opening, overmolding around the pin and the tube to from a central hub, and removing the pin to form a feed passageway within the central hub, the feed passageway being in fluid communication with an interior of the tube via the inlet opening. In an embodiment, the tube includes a plurality of radial holes along a longitudinal extent of the tube. In an embodiment, the pin has a tapered tip. In an embodiment, the pin has an outer diameter that is larger than a diameter of the inlet opening of the tube so as to form an interference fit when the pin is inserted into the inlet opening. In an embodiment, the method also includes inserting a cap on each of the opposed distal ends of the tube. In an embodiment, the cap includes an axial bore oriented to direct a sparge gas out of the axial bore in a direction generally perpendicular to sparge gas exiting though the plurality of radial holes. In an embodiment, the cap includes a bore oriented to direct a sparge gas out of the bore in a direction generally parallel to sparge gas exiting though the plurality of radial holes. In an embodiment, the cap is attached to the tube by at least one of a press fit, an adhesive and/or welding.

In yet another embodiment, a bioprocessing system is provided. The bioprocessing system includes a vessel, a flexible bioprocessing bag positionable within the vessel, and a sparger device coupled to a fluid port in the flexible bioprocessing bag, the sparger device including a sparge tube having opposed distal ends, an inlet opening, and a plurality of sparge holes along a longitudinal extent of the sparge tube between the opposed distal ends, and a central hub coupled with the sparge tube at a point intermediate the opposed distal ends of the sparge tube, the central hub having a fluid passageway in fluid communication with the sparge tube via the inlet opening. In an embodiment, the sparger device is T-shaped. In an embodiment, the sparger device further includes a cap on at least one of the opposed distal ends of the sparge tube, the cap having a throughbore in fluid communication with a central passageway of the sparge tube. In an embodiment, the throughbore is an axial throughbore oriented to direct a sparge gas out of the throughbore in a direction generally perpendicular to the sparge gas exiting though the plurality of sparge holes. In an embodiment, the throughbore is oriented to direct a sparge gas out of the throughbore in a direction generally parallel to the sparge gas exiting though the plurality of sparge holes.

In yet another embodiment, a sparger device is provided. The sparger device includes at least one sparge tube having a distal end, and a plurality of sparge holes along a longitudinal extent of the sparge tube, a hub coupled with the sparge tube, the hub having a fluid passageway in fluid communication with a central passageway of the sparge tube for providing gas to the sparge tube, and a cap on the distal end of the sparge tube, the cap having a throughbore in fluid communication with the central passageway of the sparge tube. In an embodiment, the throughbore is an axial throughbore oriented to direct a sparge gas out of the throughbore in a direction generally perpendicular to the sparge gas exiting though the plurality of sparge holes. In an embodiment, the throughbore is oriented to direct a sparge gas out of the throughbore in a direction generally parallel to the sparge gas exiting though the plurality of sparge holes.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A sparger device, comprising:
    at least one unitary sparge tube with a constant outside diameter defining a central passageway having a distal end, a plurality of sparge holes along a longitudinal extent of the sparge tube, and an inlet opening formed in the central passageway about the longitudinal extent of the sparge tube;
    a unitary hub coupled with the sparge tube while leaving the sparge tube intact, the hub having a central feed passageway in fluid communication with the central passageway of the sparge tube for providing gas to the sparge tube, wherein the central feed passageway has a larger diameter portion configured to fit a core pin and a smaller diameter portion with the smaller diameter substantially similar to that of the sparge tube central passageway, the larger diameter portion and the smaller diameter in fluid communication with the inlet opening in the sparge tube, wherein the smaller diameter portion is proximal to the inlet opening and the larger diameter portion is distal to the inlet opening, wherein the smaller diameter portion extends directly to the inlet opening without extending into the central passageway; and a cap on the distal end of the sparge tube, wherein the cap is a distinct and physical element that is separate from the sparge tube, and having a cap body formed of solid material with a recess having a uniform diameter throughout the cap body that corresponds in diameter with the constant outside diameter of the sparge tube to receive the distal end of the sparge tube therein and outward extending sidewalls defining the recess formed therebetween, each of the outward extending sidewalls advancing along an outer surface of the constant outside diameter of the sparge tube, the recess of the cap enclosing the distal end and the outward extending sidewalls enclosing a portion of the outer surface of the constant outside diameter of the sparge about the distal end, an outlet opening formed on an outer surface of the cap body, and a throughbore extending from the outlet opening directly through the cap body and to the distal end of the constant outside diameter of the sparge tube, wherein the throughbore is in fluid communication with the central passageway of the sparge tube, and wherein the outlet opening is formed on a part of the cap body that directly adjoins the distal end of the sparge tube.

2. The sparger device of claim 1, wherein:
the throughbore is an axial throughbore oriented to direct a sparge gas out of the throughbore in a direction generally perpendicular to the sparge gas exiting though the plurality of sparge holes.

3. The sparger device of claim 1, wherein:
the throughbore is oriented to direct a sparge gas out of the throughbore in a direction generally parallel to the sparge gas exiting though the plurality of sparge holes.

4. The sparger device of claim 1, wherein the hub further comprises:
a first portion extending longitudinally with the central passageway of the sparge tube and a second portion arranged perpendicularly to the first portion and the central passageway, the first portion having an opening extending from a first end to a second end thereof to receive the sparge tube therethrough, the first portion forming a sleeve that surrounds a portion of the sparge tube and the central passageway extending therethrough, the second portion having an opening therethrough that extends into the first portion and terminates at the inlet opening that provides access into the central passageway of the sparge tube, the opening in the second portion defining the central feed passageway that is in fluid communication with the central passageway of the sparge tube.

5. The sparger device of claim 1, wherein:
the unitary hub is integrally formed around the sparge tube.

6. The sparger device of claim 1, wherein:
the plurality of sparge holes are located in a top of the sparge tube; and
the inlet opening is located in a bottom of the sparge tube.

7. The sparger device of claim 2, wherein:
the throughbore includes an angle of approximately 90 degrees.

8. The sparger device of claim 1, wherein the sparge tube further comprises:
another distal end opposing the distal end of the sparge tube with the cap thereon that narrows to a point, and includes an axial opening for passage of a sparge gas.

* * * * *